US008642662B2

(12) United States Patent
Jerussi et al.

(10) Patent No.: US 8,642,662 B2
(45) Date of Patent: Feb. 4, 2014

(54) METHODS OF USING DERIVATIVES OF (−)-VENLAFAXINE

(75) Inventors: Thomas P. Jerussi, Framingham, MA (US); Chrisantha H. Senanayake, Shrewsbury, MA (US); Nandkumar N. Bhongle, Shrewsbury, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 13/481,584

(22) Filed: May 25, 2012

(65) Prior Publication Data
US 2012/0232157 A1   Sep. 13, 2012

Related U.S. Application Data

(60) Continuation of application No. 11/418,138, filed on May 5, 2006, now abandoned, which is a division of application No. 10/806,423, filed on Mar. 23, 2004, now abandoned, which is a division of application No. 10/222,815, filed on Aug. 19, 2002, now Pat. No. 6,911,479, which is a division of application No. 10/014,592, filed on Dec. 14, 2001, now Pat. No. 6,441,048, which is a division of application No. 09/450,690, filed on Nov. 30, 1999, now Pat. No. 6,342,533.

(60) Provisional application No. 60/110,488, filed on Dec. 1, 1998.

(51) Int. Cl.
  *A61K 31/135*  (2006.01)
(52) U.S. Cl.
  USPC ............ 514/649; 514/648; 564/336; 564/335
(58) Field of Classification Search
  USPC .......................... 514/649, 648; 564/336, 335
  See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,535,186 A | 8/1985 | Husbands et al. | |
| 4,604,397 A | 8/1986 | Hutchison | |
| 4,761,501 A | 8/1988 | Husbands et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,506,270 A | 4/1996 | Upton et al. | |
| 5,541,199 A | 7/1996 | Mewshaw | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,788,986 A | 8/1998 | Dodman | |
| 5,877,317 A | 3/1999 | TenBrink et al. | |
| 6,274,171 B1 | 8/2001 | Sherman et al. | |
| 6,673,838 B2 | 1/2004 | Hadfield et al. | |
| 6,689,912 B2 | 2/2004 | Weber | |
| 6,911,479 B2 | 6/2005 | Jerussi et al. | |
| 7,291,347 B2 | 11/2007 | Hadfield et al. | |
| 2003/0149112 A1 | 8/2003 | Yardley et al. | |
| 2003/0236309 A1 | 12/2003 | Hadfield et al. | |
| 2004/0181093 A1 | 9/2004 | Kim et al. | |
| 2005/0175698 A1 | 8/2005 | Diorio et al. | |

FOREIGN PATENT DOCUMENTS

| | | |
|---|---|---|
| EP | 0112669 A | 7/1984 |
| EP | 0 534 756 A | 3/1993 |
| EP | 0 639 374 A | 2/1995 |
| EP | 0654264 | 5/1995 |
| EP | 0 667 150 A | 8/1995 |
| GB | 2227743 | 8/1990 |
| WO | WO 94/00047 | 1/1994 |
| WO | WO 94/00114 | 1/1994 |
| WO | WO 97/44317 | 11/1997 |
| WO | WO 99/16417 | 4/1999 |
| WO | WO 00/32555 | 6/2000 |
| WO | WO 00/59851 | 10/2000 |
| WO | WO 00/72827 | 12/2000 |
| WO | WO 00/76955 | 12/2000 |

OTHER PUBLICATIONS

Askew, *A Simple Screening Procedure for Imipramine-Like Antidepressant Agents*, Life Sciences No. 10, Sep. 1963, pp. 725-730.
Haskins et al., *DMI, Wy-45,030, Wy-45,881 and Ciramadol Inhibit Locus Coeruleus Neuronal Activity*, European Journal of Pharmacology, 115 (1985), pp. 139-146.
Howell et al., *Pharmacokinetics of Venlafaxine and O-desmethylvenlafaxine in Laboratory Animals.* Xenobiotica, vol. 24, No. 4, 1994, pp. 315-327.
Klamerus et al., *Introduction of a Composite Parameter to the Pharmacokinetics of Venlafaxine and its Active O-Desmethyl Metabolite*, J. Clin. Pharmacol., 1992, 32:716-724.
Moyer et al., *In Vivo Antidepressant Profiles of the Novel Bicyclic Compounds Wy-45,040 and Wy-45,881*, Abstracts Society for Neuroscience, Oct. 1984, p. 261.
Moyer et al., *Subsensitivity of the Beta-Adrenergic Receptor-Linked Adenylate Cyclase System of Rat Pineal Gland Following Repeated Treatment with Desmethylimipramine and Nialamide*,Molecular Pharmacology, 19:187-193, 1981.

(Continued)

*Primary Examiner* — Sreeni Padmanabhan
*Assistant Examiner* — Jody Karol
(74) *Attorney, Agent, or Firm* — Jones Day

(57) ABSTRACT

Methods of preparing, and compositions comprising, derivatives of (−)-venlafaxine are disclosed. Also disclosed are methods of treating and preventing diseases and disorders including, but not limited to, affective disorders such as depression, bipolar and manic disorders, attention deficit disorder, attention deficit disorder with hyperactivity, Parkinson's disease, epilepsy, cerebral function disorders, obesity and weight gain, incontinence, dementia and related disorders.

5 Claims, No Drawings

(56) References Cited

OTHER PUBLICATIONS

Muth et al., *Antidepressant Biochemical Profile of the Novel Bicyclic Compounds Wy-45.030, an Ethyl Cyclohexanol Derivative*, Biochemical Pharmacology, vol. 35, No. 24, 1986, pp. 4493-4497.

Muth et al., *Biochemical, Neurophysiological, and Behavioral Effects of Wy-45,233 and Other Identified Metabolites of the Antidepressant Venlafaxine*, Drug Development Research 23:191-199, 1991.

Pento, *Drugs of the Future*, vol. 13, No. 9, 1988, pp. 839-840.

Physician's Desk Reference, 53rd Edition, 1999, pp. 3293-3302.

Sinclair et al., *The Tolerability of Venlafaxine*, Rev. Contemp. Pharmacother. 1998, 9:333-344.

Steiner et al., *Radioimmunoassay for Cyclic Nucleotides*, The Journal of Biological Chemistry, vol. 247, No. 4, Feb. 25, 1972, pp. 1106-1113.

Taft et al., Drug Metabolism and Disposition, 1997, 25(10): 1215-1218.

von Moltke et al., *Venlafaxine and Metabolites are Very Weak Inhibitors of Human Cytochrome P450-3A Isoforms*, Biol. Psychiatry 1997, 41:377-380.

Wilen et al., Strategies in Optical Resolutions, Tetrahedron, vol. 33, 1977, pp. 2725 to 2736.

Wood et al., *The Rapid Preparation of Synaptosomes, Using a Vertical Rotor*, Journal of Neurochemistry, vol. 37, No. 3, Sep. 1981, pp. 795-797.

Yardley et al., *2-Phenyl-2-(1-hydroxycycloalkyl)ethylamine Derivatives: Synthesis and Antidepressant Activity*, J. Med. Chem. 1990, vol. 33, pp. 2899-2905.

Eric A. Muth, et al., Clinical Experience with Effexor (Venlafaxine HCl): Meet the Experts, May 21, 1994, Philadelphia, PA.

Berge, S. M. et al., Journal of Pharmaceutical Sciences (1977) 66(1):1-19.

Byrn, S. et al., Pharmaceutical Research (1995) 12(7):945-954.

Egis Gyogyszergyar Nyrt, Notice of Opposition to European Patent EP 1360169, May 8, 2008. English translation provided.

Lammert, R., Notice of Opposition to European Patent EP 1360169, May 8, 2008.

Majetich, G., Tetrahedron Letters (1994) 35(47):8727-8730.

Rote Liste 2000, Preparation 71176 Trevilor.

Salzmann, K., Med. Welt. No. 9 (1970): 358-359.

Toutain, P.L. et al., Am. J. Vet. Res. (1985) 46(3):719-725.

Wolffram, S. et al., Experimental Physiology (1994) 79: 215-226.

Foreman et al., Life Science News, Amersham Life Science, US (1993) 53(3): 193-200.

Wong et al., Neuropsychopharmacology, 8(1): 23-33 (1993).

WPI Database, XP002468040 (1996).

Amsterdam, "Efficacy and Safety of Venlafaxine in the Treatment of Bipolar II Major Depressive Episode," J. of Clinical Psychopharmacology, 18(5) (1998)—abstract only.

Castello et al.., J. Pharm. Sci., 51(2):106-108 (1962).

Handbook of Pharmaceutical Excipients, 2nd Edition, Wade and Willer eds., 257-259 (1994).

Otton et al., "Venlafaxine oxidation in vitro is catalysed by CYP2D6," Br. J. Clin. Pharmacol., 41:149-156 (1996).

Remingtons: The Practice of the Science and Pharmacy, 19th Edition, Gennaro ed., 1625 (1995).

Rudaz et al., Chromatographia, 50(5/6):369-372 (1999).

Wang et al., Chirality, 4(2):84-90 (1992).

Amsterdam J., "Efficacy and Safety of Venlafaxine in the Treatment of Bipolar II Major Depressive Episode," *J. Clin. Psychopharmacology*, 18(5):414-417 (1998).

Yatham et al., "Bipolar Depression: Treatment Options," *Can. J. Psychiatry*, 42 Suppl. 2:87S-91S (1997).

METHODS OF USING DERIVATIVES OF (−)-VENLAFAXINE

This application is a continuation application of U.S. application Ser. No. 11/418,138, filed May 5, 2006, now abandoned, which is a division of U.S. application Ser. No. 10/806,423, filed Mar. 23, 2004, now abandoned, which is a division of U.S. application Ser. No. 10/222,815, filed Aug. 19, 2002, now U.S. Pat. No. 6,911,479, which is a division of U.S. application Ser. No. 10/014,592, filed Dec. 14, 2001, now U.S. Pat. No. 6,441,048, which is a division of U.S. application Ser. No. 09/450,690, filed Nov. 30, 1999, now U.S. Pat. No. 6,342,533, which claims priority to U.S. Provisional Application No. 60/110,488, filed Dec. 1, 1998, the entireties of all of which are incorporated herein by reference.

1. FIELD OF INVENTION

The invention relates to optically pure derivatives of (−)-venlafaxine, methods of their synthesis, compositions comprising them, and methods of their use.

2. BACKGROUND OF THE INVENTION

A number of nontricyclic antidepressants have recently been developed that diminish the cardiovascular and anticholinergic liability characteristic of tricyclic antidepressants. Some of these compounds are used as anti-obesity agents and have shown promise in the treatment of cerebral function disorders such as Parkinson's disease and senile dementia. See, e.g., WO 94/00047 and WO 94/00114. The nontricyclic compound, venlafaxine, chemically named (±)-1-[2-(dimethylamino)-1-(4-methoxyphenyl)ethyl]-cyclohexanol, is an antidepressant which has been studied extensively and which is described in, for example, U.S. Pat. No. 4,761,501 and Pento, J. T. *Drugs of the Future* 13(9):839-840 (1988). Its hydrochloride salt is currently commercially available in the United States under the trade name Effexor®. Effexor®, which is a racemic mixture of the (+) and (−) enantiomers of venlafaxine, is indicated for the treatment of depression.

Although venlafaxine contains an asymmetric carbon atom and is sold as a racemate, it has been reported that its (−) enantiomer is a more potent inhibitor of norepinephrine synaptosomal uptake while its (+) enantiomer is more selective in inhibiting serotonin uptake. Howell, S. R. et al. *Xenobiotica* 24(4):315-327 (1994). Furthermore, studies have shown that the ratio of the two isomers' metabolism varies not only among species, but between subjects as well. Klamerus, K. J. et al. *J. Clin. Pharmacol.* 32:716-724 (1992). In humans, venlafaxine is transformed by a saturable metabolic pathway into two minor metabolites, N-desmethylvenlafaxine and N,O-didesmethylvenlafaxine, and one major metabolite, O-desmethylvenlafaxine, as shown in Scheme I(a):

Scheme I(a)

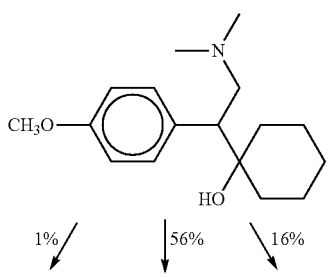

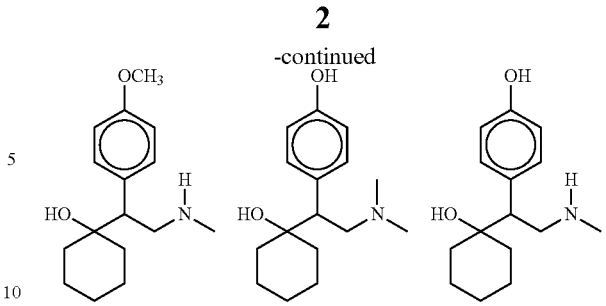

Klamerus, K. J. et al. *J. Clin. Pharmacol.* 32:716-724 (1992). All of these metabolites are racemic. In vitro studies suggest that O-desmethylvenlafaxine is a more potent inhibitor of norepinephrine and dopamine uptake than the parent compound racemic venlafaxine. Muth, F. A. et al. *Drug Develop. Res.* 23:191-199 (1991). O-desmethylvenlafaxine has also been reported to have a half-life (t½) of about 10 hours, which is approximately 2.5 times as long as that of venlafaxine. Klamerus, K. J. et al. *J. Clin. Pharmacol.* 32:716-724 (1992). Studies directed at understanding the activity of O-desmethylvenlafaxine as compared to its parent have been hampered, however, by the metabolic difference between laboratory animals and man in their exposure to venlafaxine. Howell, S. R. et al. *Xenobiotica* 24(4):315-327 (1994).

Despite the benefits of racemic venlafaxine, it has adverse effects including, but not limited to, sustained hypertension, headache, asthenia, sweating, nausea, constipation, somnolence, dry mouth, dizziness, insomnia, nervousness, anxiety, blurred or blurry vision, and abnormal ejaculation/orgasm or impotence in males. *Physicians' Desk Reference* pp. 3293-3302 (53rd ed., 1999); see also Sinclair, J. et al. *Rev. Contemp. Pharmacother.* 9:333-344 (1998). These adverse effects can significantly limit the dose level, frequency, and duration of drug therapy. It would thus be desirable to find a compound with the advantages of venlafaxine while avoiding its disadvantages.

3. SUMMARY OF THE INVENTION

This invention relates to novel pharmaceutical compositions comprising optically pure derivatives of (−)-venlafaxine such as (−)-O-desmethylvenlafaxine. The invention also relates to methods of preparing optically pure derivatives of (−)-venlafaxine with high purity and in high yield, and to methods of treating and preventing diseases and disorders which comprise the administration of one or more optically pure derivatives of (−)-venlafaxine to a human in need of such treatment or prevention.

Methods and compositions of the invention can be used to treat or prevent depression and affective disorders such as, but not limited to, attention deficit disorder and attention deficit disorder with hyperactivity. Methods and compositions of the invention are also useful in treating obesity and weight gain in a human. The invention also encompasses the treatment of cerebral function disorders including, but not limited to, senile dementia, Parkinson's disease, epilepsy, Alzheimer's disease, amnesia/amnestic syndrome, autism and schizophrenia; disorders ameliorated by inhibition of neuronal monamine reuptake; and pain, particularly chronic pain. The invention further encompasses the treatment or prevention of obsessive-compulsive disorder, substance abuse, pre-menstrual syndrome, anxiety, eating disorders and migraines. The invention finally encompasses the treatment or prevention of incontinence in humans.

The compounds and compositions of the invention possess potent activity for treating or preventing the above-described disorders while reducing or avoiding adverse effects including, but not limited to, sustained hypertension, headache, asthenia, sweating, nausea, constipation, somnolence, dry mouth, dizziness, insomnia, nervousness, anxiety, blurred or blurry vision, and abnormal ejaculation/orgasm or impotence in males. In particular, adverse effects associated with the administration of racemic venlafaxine are reduced or avoided by the use of optically pure derivatives of (−)-venlafaxine. Compositions of the invention can also exhibit long half lives as compared to racemic venlafaxine.

Although a variety of pharmaceutical salts, solvates, clatherates and/or hydrates (including anhydrous forms) of the active ingredients disclosed herein are suitable for use in the methods and compositions of the invention, the optically pure derivatives of (−)-venlafaxine are typically prepared as hydrochloride salts, and preferably as the monohydrates.

3.1. DEFINITIONS

As used herein, the term "venlafaxine" means the racemic compound (±)-1-[2-(dimethylamino)-1-(4-methoxyphenyl) ethyl]cyclohexanol.

As used herein, the terms "venlafaxine derivative" and "derivative of venlafaxine" encompass, but are not limited to, human metabolites of racemic venlafaxine. In particular, the terms "venlafaxine derivative" and "derivative of venlafaxine" mean a compound selected from the group that includes, but is not limited to: (±)-N-desmethylvenlafaxine, chemically named (±)-1-[2-(methylamino)-1-(4-methoxyphenyl)ethyl] cyclohexanol; (±)-N,N-didesmethylvenlafaxine, chemically named (±)-1-[2-(amino)-1-(4-methoxyphenyl)ethyl]cyclohexanol; (±)-O-desmethylvenlafaxine, chemically named (±)-1-[2-(dimethylamino)-1-(4-phenol)ethyl]cyclohexanol; (±)-N,O-didesmethylvenlafaxine, chemically named (±)-1-[2-(methylamino)-1-(4-phenol)ethyl]cyclohexanol; and (±)-O-desmethyl-N,N-didesmethylvenlafaxine, chemically named chemically named (±)-1-[2-(amino)-1-(4-phenol) ethyl]cyclohexanol.

As used herein, the terms "(−)-venlafaxine derivative" and "derivative of (−)-venlafaxine" encompass, but are not limited to, optically pure human metabolites of (−)-venlafaxine. In particular, the terms "(−)-venlafaxine derivative" and "derivative of (−)-venlafaxine" mean a compound selected from the group that includes, but is not limited to: optically pure (−)-N-desmethylvenlafaxine, chemically named (−)-1-[2-(methylamino)-1-(4-methoxyphenyl)ethyl]cyclohexanol; optically pure (−)-N,N-didesmethylvenlafaxine, chemically named (−)-1-[2-(amino)-1-(4-methoxyphenyl)ethyl]cyclohexanol; optically pure (−)-O-desmethylvenlafaxine, chemically named (−)-1-[2-(dimethylamino)-1-(4-phenol)ethyl]cyclohexanol; optically pure (−)-N,O-didesmethylvenlafaxine, chemically named (−)-1-[2-(methylamino)-1-(4-phenol)ethyl]cyclohexanol; and optically pure (−)-O-desmethyl-N,N-didesmethylvenlafaxine, chemically named chemically named (−)-1-[2-(amino)-1-(4-phenol)ethyl]cyclohexanol.

As used herein, the terms "(+)-venlafaxine derivative" and "derivative of (+)-venlafaxine" encompass, but are not limited to, optically pure human metabolites of (+)-venlafaxine. In particular, the terms "(+)-venlafaxine derivative" and "derivative of (+)-venlafaxine" mean a compound selected from the group that includes, but is not limited to: optically pure (+)-N-desmethylvenlafaxine, chemically named (+)-1-[2-(methylamino)-1-(4-methoxyphenyl)ethyl]cyclohexanol; optically pure (+)-N,N-didesmethylvenlafaxine, chemically named (+)-1-[2-(amino)-1-(4-methoxyphenyl)ethyl]cyclohexanol; optically pure (+)-O-desmethylvenlafaxine, chemically named (+)-1-[2-(dimethylamino)-1-(4-phenol)ethyl] cyclohexanol; optically pure (+)-N,O-didesmethylvenlafaxine, chemically named (+)-1-[2-(methylamino)-1-(4-phenol)ethyl]cyclohexanol; and optically pure (+)-O-desmethyl-N,N-didesmethylvenlafaxine, chemically named chemically named (+)-1-[2-(amino)-1-(4-phenol)ethyl]cyclohexanol.

As used herein to describe a compound, the term "substantially free of its (+) stereoisomer" means that the compound is made up of a significantly greater proportion of its (−) stereoisomer than of its optical antipode (i.e., its (+) stereoisomer). In a preferred embodiment of the invention, the term "substantially free of its (+) stereoisomer" means that the compound is made up of at least about 90% by weight of its (−) stereoisomer and about 10% by weight or less of its (+) stereoisomer. In a more preferred embodiment of the invention, the term "substantially free of its (+) stereoisomer" means that the compound is made up of at least about 95% by weight of its (−) stereoisomer and about 5% by weight or less of its (+) stereoisomer. In an even more preferred embodiment, the term "substantially free of its (+) stereoisomer" means that the compound is made up of at least about 99% by weight of its (−) stereoisomer and about 1% or less of its (+) stereoisomer. In another preferred embodiment, the term "substantially free of its (+) stereoisomer" means that the compound is made up of nearly 100% by weight of its (−) stereoisomer. The above percentages are based on the total amount of the combined stereoisomers of the compound. The terms "substantially optically pure (−)-venlafaxine derivative," "optically pure (−)-venlafaxine derivative" and "(−) isomer of venlafaxine derivative" all refer to a derivative of (−)-venlafaxine that is substantially free of its (+) stereoisomer.

As used herein, the term "pharmaceutically acceptable salts" refers to salts prepared from pharmaceutically acceptable non-toxic acids, including inorganic acids and organic acids. Suitable non-toxic acids include inorganic and organic acids such as acetic, benzenesulfonic; benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most particularly preferred is the hydrochloride salt.

As used herein, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ *Ed.* American Psychiatric Association (1997) (DSM-IV™).

As used herein, the term "a method of treating depression" means relief from the symptoms of depression which include, but are not limited to, changes in mood, feelings of intense sadness, despair, mental slowing, loss of concentration, pessimistic worry, agitation, and self-deprecation. Physical changes may also be relieved, including insomnia, anorexia, weight loss, decreased energy and libido, and abnormal hormonal circadian rhythms.

As used herein, the term "a method for treating obesity or weight gain" means reduction of weight, relief from being overweight, relief from gaining weight, or relief from obesity; all of which are usually due to extensive consumption of food.

As used herein, the term "a method of treating disorders ameliorated by inhibition of neuronal monoamine reuptake" means relief from symptoms of disease states associated with abnormal neuronal monoamine levels; such symptoms are reduced by way of neuronal monoamine reuptake inhibition. Monoamines, the reuptake of which are inhibited by the compounds or compositions of the present invention, include, but are not limited to, noradrenaline (or norepinephrine), serotonin and dopamine. Disorders treated by neuronal monoamine reuptake inhibition include, but are not limited to, Parkinson's disease and epilepsy.

As used herein, the term "method of treating Parkinson's disease" means relief from the symptoms of Parkinson's disease which include, but are not limited to, slowly increasing disability in purposeful movement, tremors, bradykinesia, rigidity, and a disturbance of posture in humans.

As used herein, the term "a method for treating cerebral function disorders" means relief from the disease states associated with cerebral function disorders involving intellectual deficits which include but are not limited to, senile dementia, Alzheimer's type dementia, memory loss, amnesia/amnestic syndrome, disturbances of consciousness, coma, lowering of attention, speech disorders, Parkinson's disease, Lennox syndrome, autism, hyperkinetic syndrome and schizophrenia. Also within the meaning of cerebral function disorders are disorders caused by cerebrovascular diseases including, but not limited to, cerebral infarction, cerebral bleeding, cerebral arteriosclerosis, cerebral venous thrombosis, head injuries, and the like and where symptoms include disturbances of consciousness, senile dementia, coma, lowering of attention, speech disorders, and the like.

The terms "obsessive-compulsive disorder," "substance abuse," "pre-menstrual syndrome," "anxiety," "eating disorders" and "migraine" are used herein in a manner consistent with their accepted meanings in the art. See, e.g., DSM-IV™. The terms "method of treating or preventing," "method of treating" and "method of preventing" when used in connection with these disorders mean the amelioration, prevention or relief from the symptoms and/or effects associated with these disorders. Without being limited by any theory, the treatment or prevention of certain of these disorders maybe related to the activity of the active ingredient(s) as inhibitors of serotonin uptake.

As used herein, the term "a method of treating or preventing incontinence" means prevention of or relief from the symptoms of incontinence including involuntary voiding of feces or urine, and dribbling or leakage or feces or urine which may be due to one or more causes including but not limited to pathology altering sphincter control, loss of cognitive function, overdistention of the bladder, hyper-reflexia and/or involuntary urethral relaxation, weakness of the muscles associated with the bladder or neurologic abnormalities.

4. DETAILED DESCRIPTION OF THE INVENTION

This invention relates to optically pure derivatives of (−)-venlafaxine such as, but not limited to, (−)-O-desmethylvenlafaxine, (−)-N-desmethylvenlafaxine, and (−)-N,O-didesmethylvenlafaxine. This invention further relates to the synthesis of optically pure (−)-venlafaxine derivatives and to compositions (e.g., pharmaceutical compositions) comprising them. The invention also relates to novel uses of the compounds disclosed herein, which constitute improvements over the use of racemic venlafaxine as well as over the optically pure isomers of venlafaxine.

One embodiment of the invention encompasses a method of treating an affective disorder in a human which comprises administering to a human in need of such treatment a therapeutically effective amount of a (−)-venlafaxine derivative, preferably (−)-O-desmethylvenlafaxine, or a pharmaceutically acceptable salt thereof, substantially free of its (+) stereoisomer. Venlafaxine derivatives, preferably (−)-O-desmethylvenlafaxine, can be used to treat an affective disorder while exhibiting a longer half life than venlafaxine and/or while avoiding or reducing adverse effects that are associated with the administration of venlafaxine.

Another embodiment of the invention encompasses a method of treating weight gain or obesity in a human which comprises administering to a human in need of weight loss or obesity therapy a therapeutically effective amount of a (−)-venlafaxine derivative, preferably (−)-O-desmethylvenlafaxine, or a pharmaceutically acceptable salt thereof, substantially free of its (+) stereoisomer, said amount being sufficient to reduce or prevent weight gain or obesity. Optically pure (−)-venlafaxine derivatives, preferably (−)-O-desmethylvenlafaxine, can be used to treat weight gain or obesity disorder while exhibiting a longer half life than venlafaxine and/or while avoiding or reducing adverse effects that are associated with the administration of venlafaxine.

Another embodiment of the invention encompasses a method of treating disorders ameliorated by neuronal monoamine reuptake inhibition in a human which comprises administering to a human a therapeutically effective amount of a (−)-venlafaxine derivative, preferably (−)-O-desmethylvenlafaxine, or a pharmaceutically acceptable salt thereof, substantially free of its (+) stereoisomer, said amount being sufficient to treat such disorders. Disorders which are ameliorated by neuronal monoamine reuptake include, but are not limited to, Parkinson's disease, epilepsy, and depression. The optically pure derivative of (−)-venlafaxine may be used to treat such disorders while avoiding or reducing adverse effects associated with the administration of venlafaxine.

Optically pure, or substantially optically pure, (−)-venlafaxine derivatives, preferably (−)-O-desmethylvenlafaxine, and compositions containing them are also useful in treating cerebral function disorders. Such disorders include, but are not limited to, senile dementia, Alzheimer's type dementia, memory loss, amnesia/amnestic syndrome, disturbance of consciousness, coma, lowering of attention, speech disorders, Parkinson's disease, Lennox syndrome, autism, hyperkinetic syndrome and schizophrenia. Cerebral function disorders may be induced by factors including, but not limited to, cerebrovascular diseases such as cerebral infarction, cerebral bleeding, cerebral arteriosclerosis, cerebral venous thrombosis, head injuries and the like and where symptoms include disturbances of consciousness, senile dementia, coma, lowering of attention, speech disorders and the like. Thus, the invention encompasses a method of treating cerebral function disorder in a human which comprises administering to a human in need of such therapy a therapeutically effective amount of (−)-venlafaxine derivative, preferably (−)-O-desmethylvenlafaxine, or a pharmaceutically acceptable salt thereof, substantially free of its (+) stereoisomer. The use of an optically pure (−)-venlafaxine derivative, preferably optically pure (−)-O-desmethylvenlafaxine, is intended to provide an improvement over the use of the parent drug venlafaxine. The optically pure derivatives of the invention are more potent and yet provide an overall improved therapeutic index over venlafaxine.

Another embodiment of the invention encompasses a method of treating pain, including chronic pain, in a human which comprises administering to a human in need of such therapy a therapeutically effective amount of (−)-venlafaxine derivative, preferably (−)-O-desmethylvenlafaxine, or a pharmaceutically acceptable salt thereof, substantially free of its (+) stereoisomer, said amount being sufficient to alleviate the human's pain.

Another embodiment of the invention encompasses a method of treating an obsessive-compulsive disorder in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating or preventing substance abuse in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating or preventing pre-menstrual syndrome in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating anxiety in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating an eating disorder in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating or preventing a migraine, or migraine headaches, in a human, which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer.

Another embodiment of the invention encompasses a method of treating or preventing incontinence in a human which comprises administering to a human in need of such therapy a therapeutically effective amount of a (−)-venlafaxine derivative, preferably (−)-O-desmethylvenlafaxine, or a pharmaceutically acceptable salt thereof, substantially free of its (+) stereoisomer. In particular, a (−)-venlafaxine derivative can be used to treat fecal incontinence, stress urinary incontinence ("SUI"), urinary exertional incontinence, urge incontinence, reflex incontinence, passive incontinence and overflow incontinence. In a preferred embodiments the human is an elder person of an age greater than 50 or a child of an age less than 13. Further, the invention encompasses the treatment of incontinence in patients with either loss of cognitive function, sphincter control or both. The invention is particularly well suited for the treatment or prevention of fecal incontinence and stress urinary incontinence.

Another embodiment of the invention encompasses a method of preparing (−)-N-desmethylvenlafaxine which comprises contacting a compound of Formula 5:

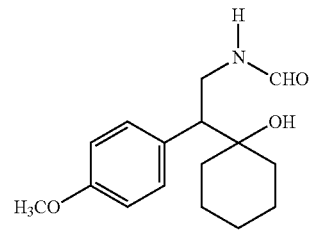

with a reductant for a time and at a temperature sufficient to form (±)-N-desmethylvenlafaxine, and isolating (−)-N-desmethylvenlafaxine therefrom. A preferred reductant is $BH_3 \cdot Me_2S$.

Another embodiment of the invention encompasses a method of preparing (−)-N,N-didesmethylvenlafaxine which comprises contacting a compound of Formula 2:

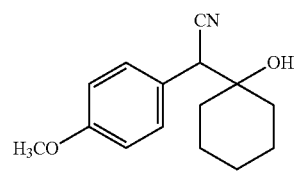

with a reductant for a time and at a temperature sufficient to form (±)-N,N-didesmethylvenlafaxine, and isolating (−)-N,N-didesmethylvenlafaxine therefrom. A preferred reductant is $CoCl_2/NaBH_4$.

Another embodiment of the invention encompasses a method of preparing (−)-O-desmethylvenlafaxine which comprises contacting (−)-venlafaxine with lithium diphenylphosphide for a time and at a temperature sufficient to form (−)-O-desmethylvenlafaxine.

Another embodiment of the invention encompasses a method of preparing (−)-O-desmethylvenlafaxine which comprises contacting (±)-venlafaxine with lithium diphenylphosphide for a time and at a temperature sufficient to form (±)-O-desmethylvenlafaxine, and isolating (−)-O-desmethylvenlafaxine therefrom.

Another embodiment of the invention encompasses substantially pure (−)-O-desmethylvenlafaxine and pharmaceutically acceptable salts, solvates, and clathrates thereof.

Another embodiment of the invention encompasses substantially pure (−)-N,O-didesmethylvenlafaxine and pharmaceutically acceptable salts, solvates, and clathrates thereof.

Another embodiment of the invention encompasses (−)-N-desmethylvenlafaxine and pharmaceutically acceptable salts, solvates, and clathrates thereof.

A final embodiment of the invention encompasses (−)-N,N-didesmethylvenlafaxine and pharmaceutically acceptable salts, solvates, and clathrates thereof.

Compounds of the invention, which can be used and prepared as described herein, are shown below in Scheme I(b):

Scheme I(b)

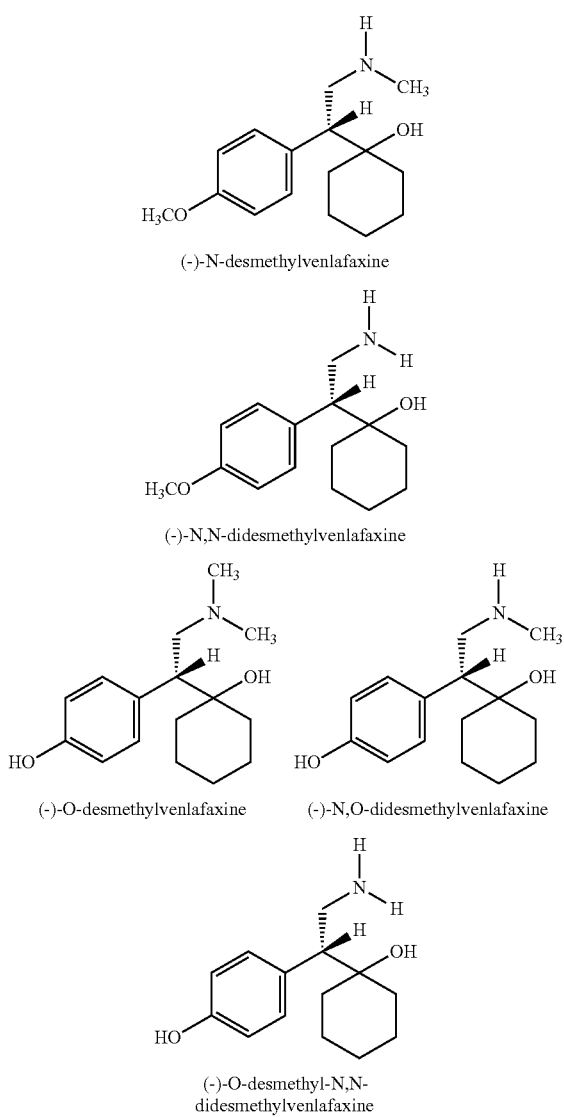

(-)-N-desmethylvenlafaxine (-)-N,N-didesmethylvenlafaxine (-)-O-desmethylvenlafaxine (-)-N,O-didesmethylvenlafaxine (-)-O-desmethyl-N,N-didesmethylvenlafaxine The synthesis of some venlafaxine derivatives has been described by Yardley, J. P. et al. *J. Med. Chem.* 33:2899-2905 (1990), the disclosure of which is hereby incorporated by reference. This method, which may be adapted for the synthesis of the compounds of this invention, is shown in Scheme II:

Scheme II

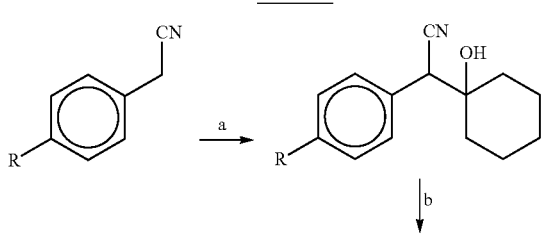

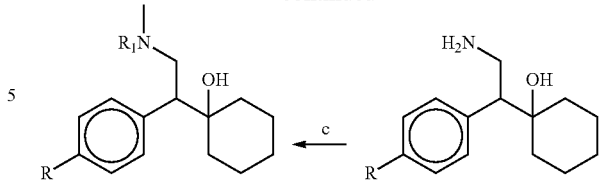

wherein R is methoxy or hydroxy, $R_1$ is hydrogen or methyl, and the reaction conditions are as follows: (a) LDA in cycloalkanone at −78° C.; (b) Rh/$Al_2O_3$, and (c) HCHO, HCOOH, $H_2O$, reflux. The (−) isomer of the racemic final product yielded by step (c) may be isolated by any method known to those skilled in the art, including high performance liquid chromatography (HPLC) and the formation and crystallization of chiral salts. See, e.g., Jacques, J., et al., *Enantiomers, Racemates and Resolutions*, (Wiley-Interscience, New York, 1981); Wilen, S. H., et al., *Tetrahedron* 33:2725 (1977); Eliel, E. L. *Stereochemistry of Carbon Compounds* (McGraw-Hill, New York, 1962); and Wilen, S. H. *Tables of Resolving Agents and Optical Resolutions* p. 268 (E. L. Eliel, Ed. Univ. of Notre Dame Press, Notre Dame, Ind., 1972). As used herein, the term "isolate" encompasses the isolation of a compound from a reaction mixture, the purification of the compound, and the optical resolution of the compound.

In a preferred method of the invention, (−)-N,N-didesmethylvenlafaxine is prepared from (±)-N,N-didesmethylvenlafaxine, which itself is preferably prepared according to the method shown in Scheme III:

Scheme III

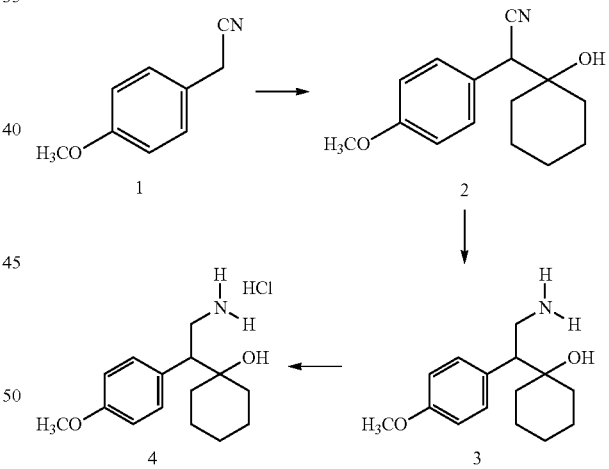

According to this method, cyclohexanone is reacted with compound 1 to provide compound 2. This reaction is preferably done in the presence of a catalyst such as, but not limited to, lithium diisopropylamide (LDA), and in an aprotic solvent such as, but not limited to, THF. The cyano group of compound 2 is subsequently contacted with a reductant to provide compound 3, (±)-N,N-didesmethylvenlafaxine. A preferred reductant is $CoCl_2$/$NaBH_4$ in methanol, although other reductants known to those skilled in the art can also be used. Salts of (±)-N,N-didesmethylvenlafaxine, such as the HCl salt (compound 4), can then be formed using reaction conditions well known in the art. (−)-N,N-didesmethylvenlafaxine can be isolated from (±)-N,N-didesmethylvenlafaxine using methods known in the art (e.g., by the formation of a chiral salt or using chiral chromatography).

Referring again to Scheme III, (−)-N,N-didesmethylvenlafaxine can alternatively be prepared from the appropriate enantiomer of compound 2. Optically pure enantiomers of compound 2 can be isolated using methods known in the art (e.g., by the formation of a chiral salt or using chiral chromatography).

In another preferred method of the invention, (−)-N-desmethylvenlafaxine is prepared from (±)-N-desmethylvenlafaxine, which itself is prepared from (±)-N,N-didesmethylvenlafaxine according to the method shown in Scheme IV:

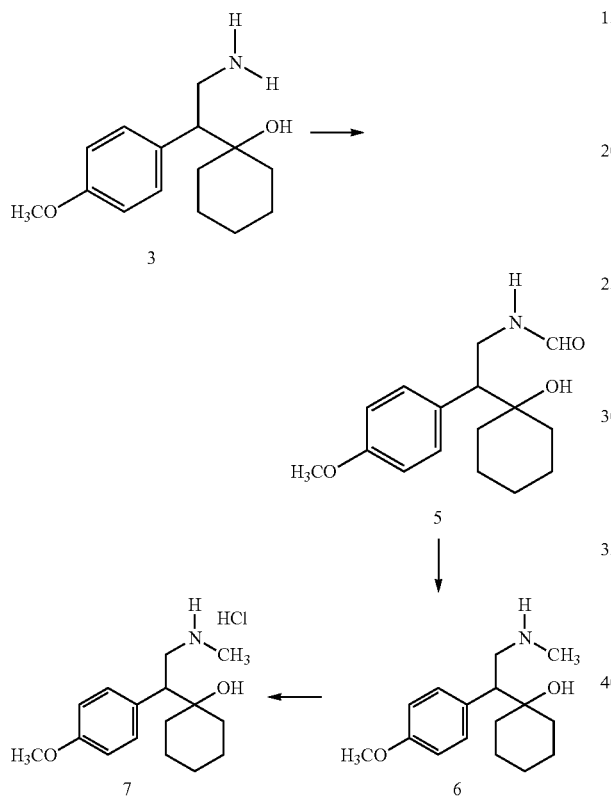

According to this method, (±)-N,N-didesmethylvenlafaxine (compound 3) is converted to compound 5 using, for example, HCO$_2$H in a solvent such as, but not limited to, toluene. The aldehyde of compound 5 is subsequently reduced to provide compound 6, (±)-N-desmethylvenlafaxine. A preferred reductant is BH$_3$.Me$_2$S in an aprotic solvent such as, but not limited to, THF. Salts of (±)-N-desmethylvenlafaxine, such as the HCl salt (compound 7), can then be formed using reaction conditions well known in the art. (−)-N-desmethylvenlafaxine can be isolated from (±)-N-desmethylvenlafaxine using methods known in the art (e.g., by the formation of a chiral salt or using chiral chromatography).

Referring again to Scheme IV, (−)-N-desmethylvenlafaxine can alternatively be prepared from the appropriate enantiomers of compounds 3 or 5. Optically pure enantiomers of compounds 3 and 5 can be isolated using methods known in the art (e.g., by the formation of a chiral salt or using chiral chromatography).

It is also possible to prepare the compounds of the invention from racemic venlafaxine, which can be prepared according to methods disclosed, for example, by U.S. Pat. No. 4,761,501 and Pento, J. T. *Drugs of the Future* 13(9):839-840 (1988), both of which are incorporated herein by reference. Optically pure (−)-venlafaxine can be isolated from the racemic mixture by conventional means such as those described above, and then selectively demethylated according to methods known to those skilled in the art. See, e.g., March, J. *Advanced Organic Chemistry* p. 361 (3$^{rd}$ ed. 1985).

In a preferred method of the invention, optically pure (−)-venlafaxine is isolated from (±)-venlafaxine according to the method shown in Scheme V:

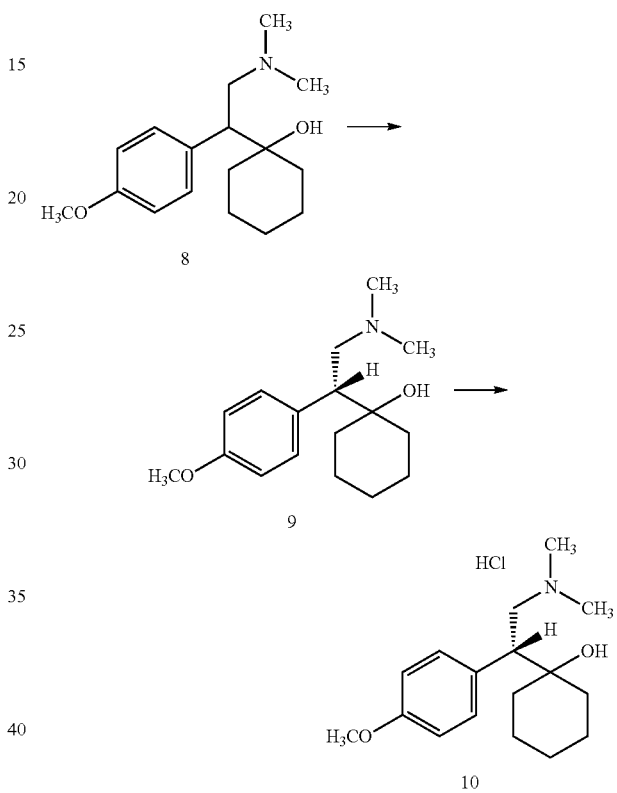

According to this method, (−)-venlafaxine (compound 9) is isolated from (±)-venlafaxine (compound 8) by forming a chiral salt using, for example, di-p-toluoyl-D-tartaric acid. Salts of (−)-venlafaxine, such as the HCl salt (compound 10), can then be formed using reaction conditions well known in the art.

Compounds of the invention are readily prepared from (−)-venlafaxine. For example, in a preferred method of the invention, (−)-O-desmethylvenlafaxine is prepared from (−)-venlafaxine as show Scheme VI:

Scheme VI

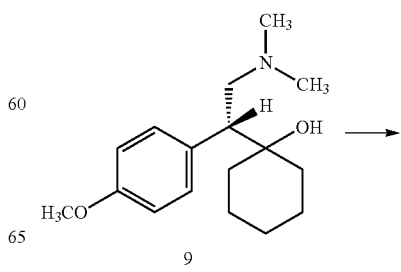

9

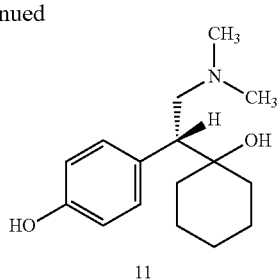

11

According to this method, the methoxy group of (−)-venlafaxine (compound 9) is converted to an alcohol to provide (−)-O-desmethylvenlafaxine (compound 11) using, for example, lithium diphenylphosphide.

Alternative methods of preparing (±)-venlafaxine HCl and (±)-O-desmethyl-venlafaxine, from which optically pure (−)-venlafaxine derivatives can be prepared using methods such as those described herein, are shown in Scheme VII:

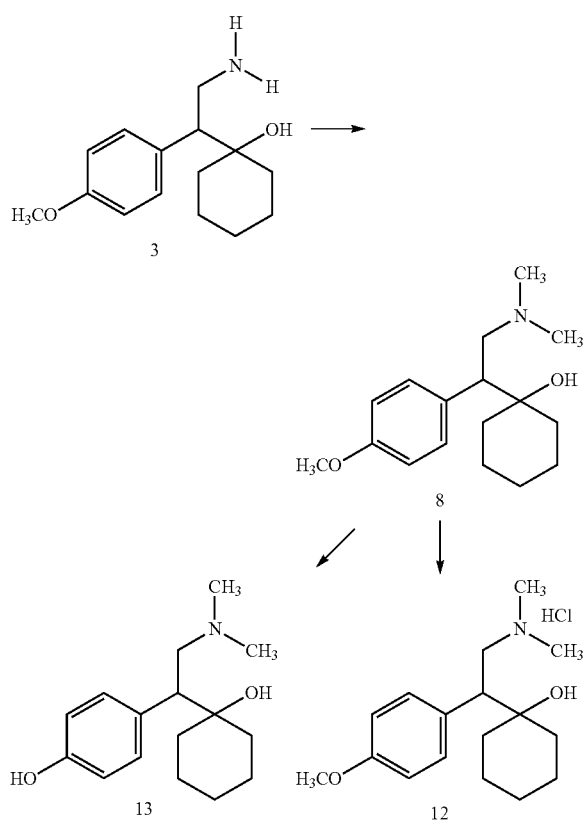

According to Scheme VII, (±)-venlafaxine (compound 8) is prepared by reacting (±)-N,N-didesmethylvenlafaxine (compound 3) with, for example, HCHO/HCO$_2$H. Compound 8 can then be converted to (±)-O-desmethylvenlafaxine (compound 13) using, for example, lithium diphenylphosphide. Alternatively, salts of (±)-venlafaxine, such as the HCl salt (compound 12), can be formed using reaction conditions well known in the art. Optically pure enantiomers of compounds 12 and 13 can be isolated using methods known to those skilled in the art (e.g., by the formation of a chiral salt or using chiral chromatography). Optically pure enantiomers of compounds 12 and 13 can also be prepared according to Scheme VII by beginning with the corresponding optically pure enantiomers of compound 8.

Utilizing the optically pure or substantially optically pure derivatives of (−)-venlafaxine in the treatment and/or mitigation of the conditions described herein results in clearer dose-related definitions of efficacy, diminished adverse effects, and accordingly an improved therapeutic index as compared to venlafaxine itself.

The magnitude of a prophylactic or therapeutic dose of a (−)-venlafaxine derivative (herein also referred to as an "active ingredient"), preferably (−)-O-desmethylvenlafaxine, in the acute or chronic management of a disease will vary with the severity of the condition to be treated and the route of administration. The dose, and perhaps the dose frequency, will also vary according to age, body weight, response, and the past medical history of the individual patient. In general, the recommended daily dose range for the conditions described herein lie within the range of from about 10 mg to about 1000 mg per day, given as a single once-a-day dose in the morning but preferably as divided doses throughout the day taken with food. Preferably, a daily dose range should be from about 50 mg to about 500 mg per day, more preferably, between about 75 mg and about 350 mg per day. In managing the patient, the therapy should be initiated at a lower dose, perhaps about 50 mg to about 75 mg, and increased if necessary up to about 250 mg to about 325 mg per day as either a single dose or divided doses, depending on the patient's global response. If a dosage is increased, it is preferably done in intervals of about 75 mg separated by at least 4 days.

Because elimination of (−)-venlafaxine derivatives from the bloodstream is dependant on renal and liver function, it is recommended that the total daily dose be reduced by at least 50% in patients with moderate hepatic impairment, and that it be reduced by 25% in patients with mild to moderate renal impairment. For patients undergoing hemodialysis, it is recommended that the total daily dose be reduced by 5% and that the dose be withheld until the dialysis treatment is completed. Because some adverse reactions have been reported for patients who took venlafaxine concurrently with, or shortly after, a monamine oxidase inhibitor, it is recommended that the (−)-venlafaxine derivatives of this invention not be administered to patients currently taking such inhibitors. In general, the concurrent administration of the compounds of this invention with other drugs, particularly other serotonin uptake inhibitors, should be done with care. See, e.g., von Moltke, L. L. et al. *Biol. Psychiatry* 41:377-380 (1997); and Sinclair, J. et al. *Rev. Contemp. Pharmacother.* 9:333-344 (1998).

The various terms "said amount being sufficient to alleviate the affective disorder," "said amount being sufficient to alleviate depression," "said amount being sufficient to alleviate attention deficit disorder," "said amount being sufficient to alleviate an obsessive-compulsive disorder", "said amount being sufficient to prevent or alleviate substance abuse", "said amount being sufficient to prevent or alleviate pre-menstrual syndrome", "said amount being sufficient to prevent or alleviate anxiety", "said amount being sufficient to prevent or alleviate an eating disorder", "said amount being sufficient to prevent or alleviate or prevent migraine", "said amount being sufficient to alleviate Parkinson's disease," "said amount being sufficient to alleviate epilepsy," "said amount being sufficient to alleviate obesity or weight gain," "an amount sufficient to achieve weight loss," "said amount being sufficient to bring about weight reduction in a human," "said amount being sufficient to alleviate pain," "said amount being sufficient to alleviate dementia," "said amount sufficient to alleviate said disorders ameliorated by inhibition of neuronal monoamine reuptake," "said amount is sufficient to alleviate cerebral function disorders" wherein said disorders are selected from the group consisting of senile dementia, Alzheimer's type dementia, memory loss, amnesia/amnestic syndrome, disturbance of consciousness, coma, lowering of attention, speech disorders, Parkinson's disease, Lennox syndrome, autism, hyperkinetic syndrome, schizophrenia, and cerebrovascular diseases, such as cerebral infarction, cerebral bleeding, cerebral arteriosclerosis, cerebral venous thrombosis, head injuries, and the like, "said amount being sufficient to treat or prevent incontinence" wherein said incontinence includes but is not limited to fecal, stress, urinary, urinary exertional, urge, reflex, passive and overflow incontinence, are encompassed by the above described dosage amounts and dose frequency schedule. Similarly, amounts sufficient to alleviate each of the above disorders but insufficient to cause adverse effects associated with venlafaxine are also encompassed by the above described dosage amounts and dose frequency schedule.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Preferred routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. A preferred transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

Other dosage forms of the invention include, but are not limited to, tablets, caplets, troches, lozenges, dispersions, suspensions, suppositories, ointments, cataplasms (poultices), pastes, powders, dressings, creams, plasters, solutions, capsules, soft elastic gelatin capsules, and patches.

In practical use, an active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, preferably without employing the use of lactose. For example, suitable carriers include powders, capsules, and tablets, with the solid oral preparations being preferred over the liquid preparations.

Because of their ease of administration, tablets and capsules represent the most advantageous oral dosage unit forms, in which case solid pharmaceutical carriers are employed. If desired, tablets can be coated by standard aqueous or non-aqueous techniques.

In addition to the common dosage forms set out above, an active ingredient can also be administered by controlled release means or delivery devices that are well known to those of ordinary skill in the art, such as those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are incorporated herein by reference. These dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency, and 3) increased patient compliance. In addition, controlled-release formulations can be used to affect the time of onset of action or other characteristics, such as blood levels of the drug, and thus can affect the occurrence of side effects.

Most controlled-release formulations are designed to initially release an amount of drug that promptly produces the desired therapeutic effect, and to gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various inducers, including, but not limited to, pH, temperature, enzymes, water, or other physiological conditions or compounds.

Pharmaceutical compositions of the invention suitable for oral administration can be presented as discrete dosage forms, such as capsules, cachets, or tablets, or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses lactose-free pharmaceutical compositions and dosage forms. Lactose is used as an excipient in venlafaxine formulations. See, e.g., *Physician's Desk Reference*®3294 (53$^{rd}$ ed., 1999). Unlike the parent drug, however, N-demethylated derivatives of (−)-venlafaxine (e.g., (−)-N-desmethylvenlafaxine and (−)-N,N-didesmethylvenlafaxine), are secondary or primary amines and may thus decompose over time when exposed to lactose. Consequently, compositions of the invention that comprise N-demethylated derivatives of (−)-venlafaxine preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising an active ingredient, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, New York, N.Y., 1995, pp. 379-80. In effect, water and heat accelerate decomposition. Thus the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms of the invention which contain lactose are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation comprising an active ingredient which method comprises admixing under anhydrous or low moisture/humidity conditions the active ingredient and an excipient (e.g., lactose), wherein the ingredients are substantially free of water. The method can further comprise packaging the anhydrous or non-hygroscopic solid formulation under low moisture conditions. By using such conditions, the risk of contact with water is reduced and the degradation of the active ingredient can be prevented or substantially reduced.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, for example, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder/filler in pharmaceutical compositions of the present invention is typically present in about 50 to about 99 weight percent of the pharmaceutical composition.

Disintegrants are used in the compositions of the invention to provide tablets that disintegrate when exposed to an aqueous environment. Too much of a disintegrant will produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form the dosage forms of the compounds disclosed herein. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, can be used in the pharmaceutical composition.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical-compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), or mixtures thereof. A lubricant can optionally be added, typically in an amount of less than about 1 weight percent of the pharmaceutical composition.

Desirably, each tablet contains from about 25 mg to about 150 mg of the active ingredient and each cachet or capsule contains from about 25 mg to about 150 mg of the active ingredient. Most preferably, the tablet, cachet, or capsule contains either one of three dosages, e.g., about 25 mg, about 50 mg, or about 75 mg of active ingredient (as scored tablets, the preferable dose form).

The invention is further defined by reference to the following examples describing in detail the preparation of the compositions of the invention. It will be apparent to those skilled in the art that many modifications, both to materials and methods, may be practiced without departing from the purpose and interest of this invention.

5. EXAMPLES

As discussed above, at least two different synthetic approaches may be utilized to obtain the compounds of this invention. A first is based upon the isolation of (−)-venlafaxine, followed by selective demethylation. In a second approach, racemic mixtures of venlafaxine derivatives are separated into their optically pure components.

5.1. Example 1

Synthesis and Resolution of (−)-Venlafaxine
1-[cyano-(4-methoxyphenyl)methyl]cyclohexanol A solution of 4-methoxybenzylnitrile (53.5 g, 0.36 mol) in 400 mL THF was cooled to −78° C. followed by slow addition of a 2.0 M THF solution of lithium diisopropylamide (200 mL, 0.40 mol) maintaining the reaction temperature below −65° C. The reaction was stirred at −78° C. for 30 minutes. Cyclohexanone (39.5 g, 0.40 mol) was added at a rate such that the reaction temperature did not rise above −65° C. After the addition reaction was stirred at −78° C. for 2 hours, then was poured into 1 L saturated aqueous $NH_4Cl$ containing ice. The mixture was stirred for 15 minutes and was extracted with ethyl acetate (4×200 mL). Combined ethyl acetate layer was washed with water (3×100 mL), brine (1×100 mL) and dried ($Na_2SO_4$). Ethyl acetate was evaporated in vacuo to give colorless solid that was trichurated with hexane. The precipitate was filtered, washed with hexane, dried in vacuo to give colorless solid (72.0 g, 80.7% yield). $^1H$ ($CDCl_3$): 7.30 and 6.90 (q, 4H), 3.80 (s, 3H), 3.75 (s, 1H), 1.55 (m, 10H); $^{13}C$ ($CDCl_3$): 159.8, 130.8, 123.8, 120.0, 114.1, 72.9, 55.5, 49.5, 34.9, 25.3, 21.6.

1-[2-amino-1-(4-methoxyphenyl)ethyl]cyclohexanol

A 3-L, three-neck flask equipped with a mechanical stirrer and a thermocouple was charged with 1-[cyano(4-methoxyphenyl)methyl]cyclohexanol (40.0 g, 0.16 mol) and 1 L methanol. To the resulting stirred solution was added cobalt chloride (42.4 g, 0.32 mol) and the reaction was stirred until a clear dark blue solution was obtained. Sodium borohydride (62.0 g, 1.63 mol) was added in small lots maintaining the reaction temperature below 35° C. A dark black precipitate was formed along with vigorous evolution of gas as soon as sodium borohydride was added. After completion of addition the slurry was stirred at room temperature for 2 hours. TLC examination indicated complete disappearance of the starting material. The reaction was cooled in ice/water and 1 L 3N HCl was added slowly. Reaction temperature was maintained below 25° C. Reaction was stirred for 30 minutes after completion of the addition. Small amount of black precipitate was still observed. Methanol was removed in vacuo followed by extraction of the aqueous layer with ethyl acetate (3×300 mL). The aqueous layer was cooled in ice/water and was basified (pH paper) by slow addition of concentrated $NH_4OH$ (~600 mL). Reaction temperature was maintained below 25° C. Reaction was extracted with ethyl acetate (4×200 mL). Combined ethyl acetate layer was washed with water (3×100 mL), brine (1×100 mL), and dried ($Na_2SO_4$). Ethyl acetate was evaporated in vacuo to give yellow gum (34.0 g, 83.6% yield). $^1H$ ($CDCl_3$): 7.20 and 6.85 (q, 4H), 3.80 (s, 3H), 3.20 (m, 2H), 2.70 (t, 3H), 2.35 (br s, 3H), 1.40 (m, 10H); $^{13}C$ ($CDCl_3$): 158.4, 132.6, 130.6, 113.7, 73.7, 56.7, 55.3, 42.4, 37.3, 34.5, 26.0, 21.9.

(±)-Venlafaxine

1-[2-amino-1-(4-methoxyphenyl)ethyl]cyclohexanol (33.0 g, 0.13 mol) was dissolved in 88% formic acid (66.0 g, 55 mL, 1.43 mol) and water (330 mL) followed by addition of 37% aqueous formaldehyde (44.4 g, 41 mL, 1.48 mol). The resulting solution was refluxed for 20 hours, cooled to room temperature and was concentrated to 150 mL, adjusted to pH 2.0 with 3N HCl, and extracted with ethyl acetate (~6×50 mL) until pink impurity was removed. The aqueous layer was cooled in ice/water and was basified by slow addition of 50% NaOH. The aqueous layer was extracted with ethyl acetate (3×75 mL). Combined ethyl acetate layer was washed with water (3×25 mL), brine (1×25 mL) and dried ($Na_2SO_4$). Ethyl acetate was evaporated in vacuo to give yellow gum that turned slowly in to pale yellow solid (34.0 g, 92.6% yield). $^1H$ ($CDCl_3$): 7.05 and 6.80 (q, 4H), 3.80 (s, 3H), 3.30 (t, 1H), 2.95 (dd, 1H), 2.35 (s, 6H), 2.30 (dd, 1H), 1.30 (m, 10H); $^{13}C$ ($CDCl_3$): 158.4, 132.9, 130.3, 113.5, 74.4, 61.4, 55.3, 51.8, 45.6, 38.2, 31.3, 26.2, 21.8, 21.5. MS (277, M+).

(±)-Venlafaxine-HCl Salt

A solution of (±)-venlafaxine (1.0 g, 3.6 mmol) in 100 mL MTBE was cooled to 0° C. and 2 mL of 15% HCl in MTBE was added to it. A colorless precipitate was formed. The reaction was stirred at 0° C. for 10 minutes. Solid was filtered, washed with MTBE, dried in vacuo to give the product as colorless solid (0.700 g, 61.9% yield). $^1H$ ($CDCl_3$): 11.40 (s, 1H), 7.15 and 6.85 (q, 4H), 4.05 (d, 1H), 3.80 (s, 3H), 3.35 (t, 1H), 3.20 (m, 2H), 2.80 (s, 3H), 2.60 (s, 3H), 1.30 (m, 10H); $^{13}C$ ($CDCl_3$): 159.0, 131.4, 130.3, 114.2, 73.7, 60.4, 55.4, 52.7, 45.3, 42.8, 36.7, 31.5, 25.5, 21.7, 21.3. MS (277, M+ for free base). % purity (HPLC): 99.62.

Tartrate Salts of Venlafaxine

To a stirred solution of (±)-venlafaxine (20.0 g, 0.072 mol) in 150 mL ethyl acetate was added a solution of di-p-toluoyl-D-tartaric acid (16.0 g, 0.041 mol) in 120 mL ethyl acetate. Mild exotherm was observed. Colorless solid started precipitating out within 15 minutes. The suspension was stirred at room temperature for 4 hours. The solid was filtered, washed with ethyl acetate, dried in vacuo to give (R)-venlafaxine-di-p-toluoyl-D-tartrate salt as colorless solid (18.0 g, 37.6% yield).

Combined mother liquors from above reaction were washed with ice-cold 1N NaOH (4×100 mL), water (3×200 mL), brine (1×100 mL), dried ($Na_2SO_4$). Ethyl acetate was evaporated in vacuo to give colorless solid (10.8 g, 0.039 mol). This solid was dissolved in 75 mL of ethyl acetate and a solution of di-p-toluoyl-L-tartaric acid (11.3 g, 0.029 mol) in 75 mL ethyl acetate was added to it. Colorless solid started precipitating out within 30 minutes. Additional amount of ethyl acetate (50 mL) was added to the slurry and it was stirred overnight at RT. The solid was filtered, washed with ethyl acetate, dried in vacuo to give (S)-venlafaxine-di-p-toluoyl-L-tartrate salt as colorless solid (13.0 g, 50.0% yield).

Crystallization of the Tartrate Salt (R)-Venlafaxine-di-p-toluoyl-D-tartrate salt (18.0 g, 0.027 mol) was suspended in 250 mL ethyl acetate/methanol (6:1) and the suspension was warmed to 60° C. until a clear solution was obtained. The solution was allowed to cool to room temperature and stirred overnight. Solid was filtered, washed with ethyl acetate/methanol (6:1), dried. This procedure was repeated two more times. After three crystallizations the product was obtained as colorless solid (5.76 g, 32.0% yield), e.e. (HPLC): >99.95.

(−)-Venlafaxine 50 mL cold 2N NaOH was added to (R)-(−)-venlafaxine-di-p-toluoyl-D-tartrate salt (5.3 g, 8.0 mmol) and the aqueous layer was extracted with ethyl acetate (3×100 mL). Combined ethyl acetate layer was washed with cold 2N NaOH (1×25 mL) and water until aqueous wash was neutral. Ethyl acetate layer was dried ($Na_2SO_4$), ethyl acetate evaporated to give (−)-venlafaxine as colorless solid (2.2 g, quantitative yield), e.e. (HPLC): >99.95. $^1$H, $^{13}$C and MS data as in (±)-venlafaxine.

(−)-Venlafaxine-HCl Salt (−)-venlafaxine-HCl salt was prepared from (−)-venlafaxine by following the procedure described for making (±)-venlafaxine-HCl salt.

(−)-Venlafaxine-HCl Salt: colorless solid, $[\alpha]_D$=−2.4 (c=0.25, EtOH), % purity (HPLC): 99.94, e.e. (HPLC): >99.99. $^1$H, $^{13}$C and MS data as in (±)-venlafaxine-HCl.

5.2. Example 2

Synthesis and Resolution of
(−)-O-desmethylvenlafaxine
(±)-O-desmethylvenlafaxine A solution of diphenylphosphine (3.0 g, 16.1 mmol) in 20 mL THF was cooled to −10° C. followed by slow addition of a 1.6 M THF solution of n-BuLi (12.7 mL, 20.2 mmol) at a rate such that reaction temperature did not rise above 0° C. The reaction was stirred at 0° C. for 30 minutes. A solution of (±)-venlafaxine (1.0 g, 3.6 mmol) in 10 mL THF was added slowly at 0° C. The reaction was stirred at 0° C. for 15 minutes and allowed to warm to room temperature and stirred for 1 hour. It was then refluxed overnight. The reaction was cooled to room temperature and was poured slowly into 30 mL cold 3N HCl maintaining the temperature below 15° C. After stirring for 10 minutes, the aqueous layer was extracted with ethyl acetate (3×30 mL). The aqueous layer was adjusted to pH 6.8-6.9 by slow addition of solid $NaHCO_3$. It was then saturated by adding NaCl and was extracted with ethyl acetate (6×30 mL). Combined ethyl acetate layer was dried ($Na_2SO_4$). Ethyl acetate was evaporated in vacuo to give colorless solid. The solid was triturated with cold ethyl acetate, filtered, washed with cold ethyl acetate to give colorless solid (0.700 g, 73.8% yield). $^1$H (DMSO, $d_6$): 9.30 (br s, 1H), 7.10 and 6.80 (q, 4H), 5.60 (br s, 1H), 3.15 (dd, 1H), 2.88 (t, 1H), 2.50 (dd, 1H), 2.30 (s, 6H), 1.35 (m, 10H); $^{13}$C (DMSO, $d_6$): 155.5, 131.7, 130.1, 114.4, 72.6, 60.4, 51.6, 45.3, 37.2, 32.4, 25.7, 21.2. MS: (264, M+1). % purity (HPLC): 99.9.

(−)-O-desmethylvenlafaxine (−)-O-desmethylvenlafaxine was prepared from (−)-venlafaxine by following the procedure described above.

(−)-O-desmethylvenlafaxine: colorless solid, $[\alpha]_D$=−35.2 (c=0.25, EtOH), % purity (HPLC): >99.99, e.e. (HPLC): >99.99. $^1$H, $^{13}$C and MS data as in (±)-O-demethylvenlafaxine.

5.3. Example 3

Synthesis of (−)-N-desmethylvenlafaxine
(±)-N-desmethylvenlafaxine

To a solution of 1-[amino(4-methoxyphenyl)ethyl]cyclohexanol (1.0 g, 4.0 mmol) in 8 mL of toluene, 96% formic acid (0.37 g, 8.0 mmol) was added and the reaction was refluxed for 4 hours. It was cooled to room temperature and poured into 40 mL saturated aqueous $NaHCO_3$. Toluene layer was separated and aqueous layer was extracted with toluene (3×15 mL). Combined toluene layer was washed with water (3×15 mL), brine (1×15 mL) and dried ($Na_2SO_4$). Toluene was evaporated in vacuo to give crude N-formyl compound as yellow gum (0.930 g, 83.8% yield). $^1$H ($CDCl_3$): 7.95 (s, 1H), 7.15 and 6.85 (q, 4H), 5.80 (s, 1H), 4.10 (m, 1H), 3.80 (s, 3H), 3.50 (s, 1H), 2.80 (dd, 1H), 1.50 (m, 10H); $^{13}$C ($CDCl_3$): 161.4, 158.8, 131.0, 130.7, 113.9, 73.0, 55.3, 54.2, 38.1, 36.1, 35.6, 25.6, 21.9, 21.8. (Impurity: 164.5, 129.0, 128.0, 125.0, 56.5, 42.0, 36.5, 35.5). MS (277, M+).

To a solution of crude N-formyl compound (0.585 g, 2.1 mmol) in 6 mL THF was added $BH_3.Me_2S$ (0.480 g, 0.63 mL of 10 M solution, 6.3 mmol) slowly at 0° C. The reaction was allowed to warm to room temperature and then was refluxed for 5 hours. It was cooled to 0° C. and 5 mL of methanol was added very carefully controlling the temperature below 10° C. The reaction was stirred for 10 minutes and volatiles were evaporated off. Residue was partitioned between 3N HCl (20 mL) and ethyl acetate (20 mL). Organic layer was separated and aqueous layer was extracted with ethyl acetate (3×15 mL). Aqueous layer was cooled to 0° C. and was basified by slow addition of conc. $NH_4OH$. Aqueous layer was saturated with NaCl and was extracted with ethyl acetate (3×20 mL). Combined ethyl acetate layer was dried ($Na_2SO_4$), ethyl acetate was evaporated in vacuo to give colorless oil (0.493 g, 88.8% yield). $^1$H ($CDCl_3$): 7.15 and 6.85 (q, 4H), 3.80 (s, 3H), 3.25 (dd, 1H), 2.95 (dd, 1H), 2.82 (dd, 1H), 2.45 (s, 3H), 1.40 (m, 10H); $^{13}$C ($CDCl_3$): 158.4, 133.0, 130.5, 113.7, 73.9, 55.4, 53.8, 53.0, 37.8, 36.5, 33.7, 26.0, 21.9.

(±)-N-desmethylvenlafaxine-HCl Salt

To a solution of crude (±)-N-demethyl venlafaxine (0.450 g, 1.7 mmol) in 25 mL MTBE was added 1 mL of 15% HCl in MTBE at 0° C. The resulting slurry was stirred at 0° C. for 15 minutes, filtered, solid was washed with MTBE, dried in vacuo to give the product as colorless solid (0.380 g, 74.2% yield). $^1$H ($CDCl_3$): 9.10 (br d, 1H), 7.15 and 6.85 (q, 4H), 3.80 (m & s, 4H), 3.35 (dd, 1H), 3.15 (m, 1H), 2.70 (t, 3H), 1.30 (m, 10H); $^{13}$C ($CDCl_3$): 159.0, 130.71, 130.4, 114.0, 74.7, 55.4, 52.8, 50.9, 37.0, 34.1, 30.9, 25.5, 21.4. % Purity (HPLC): 98.81.

(−)-N-desmethylvenlafaxine

Resolution of optically pure (−)-N-desmethylvenlafaxine may be performed using the methods described herein. If chiral salts are to be used, the amine is preferably protected before formation of the salt. Suitable means of protecting the amines are known to those skilled in the art and include, for example, reaction with phenacylsulfonyl chloride to yield the corresponding sulfonamide, which can be removed after isolation of the optically pure enantiomer with zinc and acetic acid. See, e.g., March, J. *Advanced Organic Chemistry* p. 445 (3$^{rd}$ ed. 1985).

5.4. Example 4

Synthesis of (±)-N,N-didesmethylvenlafaxine-HCl Salt

To a solution of 1-[amino(4-methoxyphenyl)ethyl]cyclohexanol (0.750 g, 3.0 mmol) in 75 mL MTBE was added 2 mL of 15% HCl in MTBE. The reaction was stirred at 0° C. for 15 minutes. It was then evaporated to dryness and the residue was trichurated with MTBE/hexane (6:4). Solid was filtered, washed with MTBE/hexane (6:4). The solid was suspended in cold MTBE, filtered, washed with cold MTBE, dried in vacuo to give the product as colorless solid (0.450 g, 52.3% yield). $^1$H (DMSO, d$_6$)): 7.80 (br s, 2H), 7.20 and 6.90 (q, 4H), 4.50 (br s, 1H), 3.80 (s, 3H), 3.40 (m, 1H), 3.10 (m, 1H), 2.90 (m, 1H), 1.35 (m, 10H); $^{13}$C (DMSO, d$_6$): 158.3, 130.7, 130.0, 113.5, 71.7, 54.9, 52.6, 36.3, 33.6, 26.8, 25.3, 21.4, 21.1. % Purity (HPLC): 99.3.

5.5. Example 5

Synthesis of (±)-O-desmethyl-N,N-didesmethylvenlafaxine

To a solution of diphenylphosphine (22.2 g, 0.12 mol) in 175 ml THF was added a 1.6 M THF solution of n-BuLi (94 mL, 0.15 mol) slowly maintaining the reaction temperature between −10° C. to 0° C. After the addition reaction was stirred at 0° C. for 30 minutes. A solution of (±)-N,N-didemethylvenlafaxine 13 (5.4 g, 0.021 mol) in 55 mL THF was added slowly at 0° C. The reaction mixture was stirred at 0° C. for 30 minutes and allowed to warm to room temperature and stirred at room temperature for 1 hour. It was then refluxed overnight. After cooling the reaction mixture to room temperature, it was poured slowly into 250 mL of 3N HCl while the temperature was maintained below 15° C. After stirring for 30 minutes, the aqueous layer was extracted with methylene chloride (3×200 mL). The aqueous layer was adjusted to pH 6.8-6.9 by slow addition of concentrated NH$_4$OH at 15° C. and was extracted with methylene chloride (3×100 mL). The aqueous layer was then evaporated to dryness to give a colorless solid. This colorless solid was suspended in 400 mL methylene chloride/methanol (7:3) and was stirred for 1 hour. The insolubles were filtered off, washed with methylene chloride/methanol (7:3). The filtrate was evaporated off to give colorless solid. 6.0 g of the colorless solid was chromatographed on silica gel. Elution with methylene chloride/methanol (9:1→8.5:1.5) afforded the product as a colorless solid (1.5 g). $^1$H (DMSO, d$_6$): 8.1 (br s, exchangeable, 1H), 6.95 and 6.75 (q, 4H), 4.6 (m, exchangeable, 2H), 3.3 (m, 1H), 2.9 (m, 2H), 1.2 (m, 10H); $^{13}$C (DMSO, d$_6$): 156.8, 130.5, 128.5, 115.2, 72.0, 52.1, 48.6, 36.6, 33.6, 25.6, 21.7, 21.3. % Purity (HPLC): 97.4%.

5.6. Example 6

Determination of Potency and Specificity

Several methods useful for the determination of the potency and specificity of the compounds of this invention are disclosed in the literature. See, e.g., Haskins, J. T. et al. *Euro. J. Pharmacol.* 115:139-146 (1985). Methods that have been found particularly useful are disclosed by Muth, E. A. et al. *Biochem. Pharmacol.* 35:4493-4497 (1986) and Muth, E. A. et al. *Drug Develop. Res.* 23:191-199 (1991), both of which are incorporated herein by reference.

5.6.1 Receptor Binding

Determination of receptor binding of the compounds of this invention preferably is performed by the methods disclosed by Muth et al., and using the protocols summarized below in Table I.

TABLE I

Receptor Binding Protocols

| Receptor | $^3$H-Ligand | Ligand Molarity (nM) | Specific activity (Ci/mmol) | Buffer | Incubation Time | Temp. (° C.) | Displacing agent |
|---|---|---|---|---|---|---|---|
| Dopamine-2 | Spiperone | 0.3 | 20-40 | * a | 10 min | 37° | 1 mM (+) butaclamol |
| Adrenergic | WB 4101 | 0.5 | 15-30 | 50 mM Tris-HCl pH 7.7 | 30 min | 25° | 10 mM norepinephrine bitartrate |
| Muscarinic cholinergic | Quinuclindinyl benzilate | 0.06 | 30-60 | 50 mM Tris-HCl pH 7.7 | 1 hr | 25° | 100 mM oxotremorine |
| Histamine-1 | Pyrilamine | 2.0 | <20 | 50 mM Phosphate pH 7.5 | 30 min | 25° | 10 mM chlorpheniramine maleate |
| Opiate | Naloxone | 1.3 | 40-60 | 50 nM Tris-HCl pH 7.4 | 30 min | 0-4° | 2 mM morphine | a 50 mM Tris HCl, 120 mM NaCl, 5 mM KCl, 1 mM CaCl$_2$, 1 mM MgCl$_2$, 0.1% ascorbic acid, 10 mM pargyline HCl, pH 7.1.

The tissue homogenates used are preferably whole brain except cerebellum (histamine-1 and opiate binding), cortex ($\alpha_1$ adrenergic receptor binding, monoamine uptake); and striatum (dopamine-2 and muscarinic cholinergic receptor binding).

5.6.2 Synaptosomal Uptake Studies

These studies may be performed using the modified methodology of Wood, M. D., and Wyllie, M. G. *J. Neurochem.* 37:795-797 (1981) as described in Muth et al. *Biochem. Pharmacol.* 35:4493-4497 (1986). Briefly a P2 pellet is prepared from fresh rat brain tissue by sucrose density gradient centrifugation using a vertical rotor. For uptake studies, all components are dissolved in the following buffer: 135 mM NaCl, 5 mM KCl, 1.2 mM $MgCl_2$, 2.5 mM $CaCl_2$, 10 mM glucose, 1 mM ascorbic acid, 20 mM Tris, pH 7.4, gassed with $O_2$ for 30 min prior to use. Various concentrations of test drug are preincubated with 0.1 μM [$^3$H]dopamine or 0.1 μM [$^3$H]norepinephrine (130,000 dpm/tube) and 0.1 μM [$^{14}$C]serotonin (7,500 dpm/tube) in 0.9 ml buffer for 5 min at 37° C. One-tenth milliliter of synaptosomal preparation is added to each tube and incubated for a further 4 min at 37° C. The reaction is then terminated by the addition of 2.5 ml buffer, after which the mixture was filtered under vacuum using cellulose acetate filters (0.45 μM pore size). The filters are then counted in a scintillation counter, and the results are expressed as pmoles uptake/mg protein/min. The $IC_{50}$ values for uptake inhibition are calculated by linear regression of logit [percent of $Na^+$-dependent uptake] vs. long [concentration of test drug].

5.6.3. Reversal of Reserpine-Induced Hypothermia

Reversal of reserpine-induced hypothermia in male CF-1 mice (20-25 g., Charles River) may be performed according to an adaptation of the method of Askew, B. *Life Sci.* 1:725-730 (1963). Test compounds, suspended or solubilized in 0.25% Tween80® in water, are then administered i.p. at several dose levels to male mice (8/dose level) who had been treated 18 hr previously with 45.0 mg/kg reserpine s.c. A vehicle control group is run simultaneously with drug groups. Test compounds, vehicle, and reserpine are administered at a volume of 0.01 ml/g. Reserpine is solubilized by the addition of a small amount (approximately 4 drops) of concentrated acetic acid and then brought to the proper volume by the addition of distilled water. Rectal temperatures are recorded by a Yellow Springs Instruments thermistor probe at a dept of 2 cm. Measurements are taken 18 hr after reserpine pretreatment and at hourly intervals for 3 hr following administration of either test compound or vehicle.

Rectal temperatures for all time periods are subjected to a two-way analysis of variance for repeated measures with subsequent Dunnett's comparison to control values to determine the minimum effective dose (MED) for antagonizing reserpine-induced hypothermia.

5.6.4. Induction of Rat Pineal Noradrenergic Subsensitivity

Suitable rats are male Sprague-Dawley rats (250-300 g, Charles River) which should be maintained in continuous light throughout all experiments so as to attenuate the diurnal fluctuation in beta-adrenergic receptor density in the pineal gland and to maintain a consistent supersensitive response to noradrenergic agonists. Moyer, J. A. et al. *Soc. Neurosci. Abstract* 10:261 (1984). After 2 days of continuous light exposure, the rats are then injected twice daily with either saline or test compound (10 mg/kg i.p.) for 5 days (total of 9 injections). Another group of rats should receive saline injections twice daily for 4 days followed by a single injection of test compound (10 mg/kg i.p.) on the 5th day. One hour following the final injection of test compound or saline, animals are administered either 0.1% ascorbic acid (controls), or isoproterenol (2 μmol/kg i.p. in 0.1% ascorbic acid). Rats are decapitated 2.5 minutes later, the time at which preliminary experiments have shown that the isoproterenol-induced increases in cyclic AMP levels in pineal glands are maximal. Moyer. J. A. et al. *Mol. Pharmacol.* 19:187-193 (1981). Pineal glands are removed and frozen on dry ice within 30 seconds to minimize any post-decapitation increase in cAMP concentration.

Prior to radioimmunoassay for cAMP, the pineal glands are placed in 1 ml of ice-cold 2.5% perchloric acid and sonicated for approximately 15 seconds. The sonicate is then centrifuged at 49.000 g for 15 min at 4° C. and then resulting supernatant fluid is removed, neutralized with excess $CaCO_3$, and centrifuged at 12,000 g for 10 min at 4° C. The cAMP content of the neutralized extract may be measured by a standard radioimmunoassay using $^{125}$I-labeled antigen and antiserum (New England Nuclear Corp., Boston, Mass.). Steiner, A. L. et al. *J. Biol. Chem.* 247:1106-1113 (1972). All unknown samples should be assayed in duplicate and compared to standard solutions of cAMP prepared in a 2.5% perchloric acid solution that had been neutralized with $CaCO_3$. Results are expressed as pmol cAMP/pineal, and statistical analyses are performed by analysis of variance with subsequent Student-Newman-Keuls tests.

5.6.5. Single Unit Electrophysiology

The firing rates of individual neurons of the locus coeruleus (LC) or dorsal raphe nucleus (DR) in the chloral-hydrate anesthetized rat are measured using single-barreled glass micro-electrodes as previously described for the L C. Haskins, J. T. et al. *Eur. J. Pharmacol.* 115:139-146 (1985). Using the stereotaxic orientation of Konig, J. F. R., and Klippel, R. A. *The rat brain: A stereotaxic atlas of the forebrain and lower parts of the brain stem* Baltimore: Williams and Wilkins (1963), the electrode tips should be lowered via a hydraulic microdrive from a point 1.00 mm above the locus coeruleus (AP 2.00 mm caudal to the interaural line and 1.03 mm lateral to midline). Drugs are administered i.v. through a lateral tail vein cannula. Only one cell should be studied in each rat in order to avoid residual drug effects.

5.7. Example 7

Oral Formulation

The pharmaceutical compositions of this invention may be administered in a variety of ways. Oral formulations are of the easiest to administer.

5.7.1. Hard Gelatin Capsule Dosage Forms

Table II provides the ingredients of suitable capsule forms of the pharmaceutical compositions of this invention.

TABLE II

| Component | 25 mg capsule | 50 mg capsule | 100 mg capsule |
| --- | --- | --- | --- |
| (−)-O-desmethyl-venlafaxine | 25 | 50 | 100 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient (optically pure (−)-venlafaxine derivative) is sieved and blended with the excipients listed. The mixture is filled into suitably sized two-piece hard gelatin capsules using suitable machinery and methods well known in the art. See *Remington's Pharmaceutical Sciences,* 16th or 18th Editions, each incorporated herein in its entirety by reference thereto. Other doses may be prepared by altering the fill weight and, if necessary, by changing the capsule size to suit. Any of the stable hard gelatin capsule formulations above may be formed.

5.7.2. Compressed Tablet Dosage Forms

The ingredients of compressed tablet forms of the pharmaceutical compositions of the invention are provided in Table III.

TABLE III

| Compressed Tablet Unit Dosage Forms | | | |
| --- | --- | --- | --- |
| Component | 25 mg capsule | 50 mg capsule | 100 mg capsule |
| (−)-O-desmethyl-venlafaxine | 25 | 50 | 100 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient is sieved through a suitable sieve and blended with the excipients until a uniform blend is formed. The dry blend is screened and blended with the magnesium stearate. The resulting powder blend is then compressed into tablets of desired shape and size. Tablets of other strengths may be prepared by altering the ratio of the active ingredient to the excipient(s) or modifying the table weight.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating bipolar and manic conditions comprising administering to a human a therapeutically effective amount of a (−)-venlafaxine derivative, or a pharmaceutically acceptable salt thereof, wherein the (−)-venlafaxine derivative comprises less than 10% by weight of its (+) stereoisomer.

2. The method of claim 1, wherein the (−) venlafaxine derivative is (−)-O-desmethylvenlafaxine, (−)-N-desmethylvenlafaxine, (−)-N,O-didesmethylvenlafaxine, (−)-N,N-didesmethylvenlafaxine, or (−)-O-desmethyl-N,N-didesmethylvenlafaxine.

3. The method of claim 2, wherein the (−)-venlafaxine derivative is (−)-O-desmethylvenlafaxine.

4. The method of claim 1, wherein the (−)-venlafaxine derivative comprises less than 5% by weight of its (+) stereoisomer.

5. The method of claim 1, wherein the (−)-venlafaxine derivative comprises less than 1% by weight of its (+) stereoisomer.

* * * * *